US008729317B2

(12) United States Patent
Jevtic et al.

(10) Patent No.: US 8,729,317 B2
(45) Date of Patent: *May 20, 2014

(54) ETHANOL MANUFACTURING PROCESS OVER CATALYST WITH CESIUM AND SUPPORT COMPRISING TUNGSTEN OR OXIDES THEREOF

(75) Inventors: Radmila Jevtic, Pasadena, TX (US); Victor J. Johnston, Houston, TX (US); Heiko Weiner, Pasadena, TX (US); Zhenhua Zhou, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 168 days.

This patent is subject to a terminal disclaimer.

(21) Appl. No.: 13/397,314

(22) Filed: Feb. 15, 2012

(65) Prior Publication Data
US 2013/0211152 A1 Aug. 15, 2013

(51) Int. Cl.
C07C 29/149 (2006.01)

(52) U.S. Cl.
USPC ........................................................ 568/885

(58) Field of Classification Search
USPC ........................................................ 568/885
See application file for complete search history.

(56) References Cited

U.S. PATENT DOCUMENTS

| | | | |
|---|---|---|---|
| 1,315,544 A | 9/1919 | Curme, Jr. | |
| 1,892,742 A | 1/1933 | Walter et al. | |
| 2,192,137 A | 2/1940 | Kvalnes | |
| 2,549,416 A | 4/1951 | Brooks | |
| 3,466,334 A | 9/1969 | Young et al. | |
| 3,864,284 A | 2/1975 | Clippinger et al. | |
| 3,981,923 A | 9/1976 | Stouthamer et al. | |
| 4,310,712 A | 1/1982 | Langley | |
| 4,398,039 A | 8/1983 | Pesa et al. | |
| 4,456,775 A | 6/1984 | Travers et al. | |
| 4,465,854 A | 8/1984 | Pond et al. | |
| 4,481,146 A | 11/1984 | Leupold et al. | |
| 4,514,515 A | 4/1985 | Travers et al. | |
| 4,517,391 A | 5/1985 | Schuster et al. | |
| 4,692,218 A | 9/1987 | Houben et al. | |
| 4,754,074 A | 6/1988 | Hussmann | |
| 4,777,303 A | 10/1988 | Kitson et al. | |
| 4,804,791 A | 2/1989 | Kitson et al. | |
| 4,886,905 A | 12/1989 | Larkins et al. | |
| 4,902,823 A | 2/1990 | Wunder et al. | |
| 4,990,655 A | 2/1991 | Kitson et al. | |
| 5,008,235 A | 4/1991 | Wegman et al. | |
| 5,015,786 A | 5/1991 | Araki et al. | |
| 5,103,066 A | 4/1992 | Dessau | |
| 5,149,680 A | 9/1992 | Kitson et al. | |
| 5,243,095 A | 9/1993 | Roberts et al. | |
| 5,391,291 A | 2/1995 | Winquist et al. | |
| 5,502,248 A | 3/1996 | Funk et al. | |
| 5,821,111 A | 10/1998 | Gaddy et al. | |
| 5,861,530 A | 1/1999 | Atkins et al. | |
| 5,942,460 A | 8/1999 | Garland et al. | |
| 5,973,193 A | 10/1999 | Crane et al. | |
| 6,204,417 B1 | 3/2001 | Fischer et al. | |
| 6,232,352 B1 | 5/2001 | Vidalin et al. | |
| 6,265,618 B1 | 7/2001 | Zoeller et al. | |
| 6,486,366 B1 | 11/2002 | Ostgard et al. | |
| 6,495,730 B1 | 12/2002 | Konishi et al. | |
| 6,627,770 B1 | 9/2003 | Cheung et al. | |
| 6,685,754 B2 | 2/2004 | Kindig et al. | |
| 6,693,213 B1 | 2/2004 | Kolena et al. | |
| 6,765,110 B2 | 7/2004 | Warner et al. | |
| 6,768,021 B2 | 7/2004 | Horan et al. | |
| 6,867,164 B2 | 3/2005 | Obana et al. | |
| 6,906,228 B2 | 6/2005 | Fischer et al. | |
| 6,933,414 B1 | 8/2005 | Stauffer | |
| 7,109,385 B2 | 9/2006 | Tatake et al. | |
| 7,208,624 B2 | 4/2007 | Scates et al. | |
| 7,375,049 B2 | 5/2008 | Hayes et al. | |
| 7,947,746 B2 | 5/2011 | Daniel et al. | |
| 7,964,379 B2 | 6/2011 | Verser et al. | |
| 7,994,368 B2 | 8/2011 | Johnston et al. | |
| 2003/0013908 A1 | 1/2003 | Horan et al. | |
| 2003/0077771 A1 | 4/2003 | Verser et al. | |
| 2003/0114719 A1 | 6/2003 | Fischer et al. | |
| 2004/0232049 A1 | 11/2004 | Dath et al. | |
| 2006/0106246 A1 | 5/2006 | Warner et al. | |
| 2007/0031954 A1 | 2/2007 | Mairal et al. | |
| 2007/0270511 A1 | 11/2007 | Melnichuk et al. | |
| 2008/0193989 A1 | 8/2008 | Verser et al. | |
| 2008/0207953 A1 | 8/2008 | Houssin et al. | |
| 2008/0257784 A1 | 10/2008 | Dath et al. | |
| 2009/0023192 A1 | 1/2009 | Verser et al. | |

(Continued)

FOREIGN PATENT DOCUMENTS

| | | |
|---|---|---|
| CN | 102228831 | 11/2011 |
| CN | 102229520 | 11/2011 |

(Continued)

OTHER PUBLICATIONS

International Search Report and Written Opinion mailed Mar. 21, 2012 in corresponding International Application No. PCT/US2012/066642.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

T. Yokoyama et al., "Carboxylic Acids and Derivatives", Fine Chemicals through Heterogenous Catalysis, pp. 370-379, 1982.

Pestman et al., The formation of ketones and aldehydes from carboxylic acids, structure-activity relationship for two competitive reactions, Journal of Molecular Catalysis A: Chemical 103 Jun. 14, 1995, 175-180.

(Continued)

Primary Examiner — Elvis O Price

(57) ABSTRACT

The present invention relates to a process for producing product comprising ethanol which comprises contacting a feedstock comprising acetic acid and hydrogen in a reaction zone at hydrogenation conditions with a catalyst composition comprising at least one active metal that may include a Group VIII metal and tin and from 0.01 to 0.5 wt. % cesium on a support comprising tungsten or oxides thereof.

23 Claims, No Drawings

(56) References Cited

U.S. PATENT DOCUMENTS

| | | |
|---|---|---|
| 2010/0029980 A1 | 2/2010 | Johnston et al. |
| 2010/0029996 A1 | 2/2010 | Danjo et al. |
| 2010/0121114 A1 | 5/2010 | Johnston et al. |
| 2010/0196789 A1 | 8/2010 | Fisher et al. |
| 2010/0197959 A1 | 8/2010 | Johnston et al. |
| 2010/0197985 A1 | 8/2010 | Johnston et al. |
| 2010/0249479 A1 | 9/2010 | Berg-Slot et al. |
| 2010/0273229 A1 | 10/2010 | Verser et al. |
| 2011/0082322 A1 | 4/2011 | Jevtic et al. |
| 2011/0098501 A1 | 4/2011 | Johnston et al. |
| 2011/0185628 A1 | 8/2011 | Johnston et al. |

FOREIGN PATENT DOCUMENTS

| | | |
|---|---|---|
| EP | 0104197 | 4/1984 |
| EP | 0167300 | 1/1986 |
| EP | 0175558 | 3/1986 |
| EP | 0400904 | 5/1990 |
| EP | 0372847 | 6/1990 |
| EP | 0456647 | 11/1991 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| GB | 823514 | 11/1959 |
| WO | WO 83/03409 | 10/1983 |
| WO | WO 2009/009320 | 1/2009 |
| WO | WO 2009/063174 | 5/2009 |
| WO | WO 2009/063176 | 5/2009 |
| WO | WO 2009/077719 | 6/2009 |
| WO | WO 2009/077720 | 6/2009 |
| WO | WO 2009/077725 | 6/2009 |
| WO | WO 2009/077729 | 6/2009 |
| WO | WO 2009/086839 | 7/2009 |
| WO | WO 2009/103948 | 8/2009 |
| WO | WO 2010/014145 | 2/2010 |
| WO | WO 2010/014146 | 2/2010 |
| WO | WO 2010/055285 | 5/2010 |
| WO | WO 2011/053365 | 5/2011 |
| WO | WO 2012/149137 A1 | 11/2012 |

OTHER PUBLICATIONS

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Ordóñez et al., The role of metal and support sites on the hydrogenation of acetic acid on Ru-based catalysts, 21ST NAM San Francisco, CA, Jun. 10, 2009.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Claus, et al., "Selective Hydrogenolysis of Methyl and Ethyl Acetate in the Gas Phase on Copper and Supported Group VIII Metal Catalysts", Applied Catalysis A, 79, 1991, pp. 1-18.

ETHANOL MANUFACTURING PROCESS OVER CATALYST WITH CESIUM AND SUPPORT COMPRISING TUNGSTEN OR OXIDES THEREOF

FIELD OF THE INVENTION

The present invention relates to processes for manufacturing ethanol from acetic acid. More specifically, the present invention relates to a process comprising hydrogenating acetic acid in the presence of a catalyst comprising one or more active metals and cesium on a support comprising tungsten or oxides thereof. The one or more active metals may comprise palladium, platinum, nickel, cobalt, rhenium, tin, zinc, and combinations thereof.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulose materials, such as corn or sugar cane. Conventional methods for producing ethanol from organic feedstocks, as well as from cellulose materials, include the acid-catalyzed hydration of ethylene, methanol homologation, direct alcohol synthesis, and Fischer-Tropsch synthesis. Instability in organic feedstock prices contributes to fluctuations in the cost of conventionally produced ethanol, making the need for alternative sources of ethanol production all the greater when feed stock prices rise. Starchy materials, as well as cellulose materials, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. The reduction of various carboxylic acids over metal oxides has been proposed by EP 0175558 and U.S. Pat. No. 4,398,039. A summary of some of the developmental efforts for hydrogenation catalysts for conversion of various carboxylic acids is provided in Yokoyama, et al., "Carboxylic acids and derivatives" in: *Fine Chemicals Through Heterogeneous Catalysis*, 2001, 370-379.

U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising platinum and rhenium. U.S. Pat. No. 5,149,680 describes a process for the catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes a process for the productions of alcohols by the hydrogenation of carboxylic acids in the presence of a catalyst that comprises a first component which is either molybdenum or tungsten and a second component which is a noble metal of Group VIII on a high surface area graphitized carbon support. U.S. Pat. No. 4,804,791 describes another process for the production of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process using a predominantly cobalt-containing catalyst.

U.S. Pat. No. 7,375,049 describes a catalyst for the dehydrogenation and hydrogenation of hydrocarbons which comprises at least one first metal and at least one second metal bound to a support material. The first metal comprises at least one transition metal, suitably a platinum group metal. Tin is preferred and exemplified as the second metal. The support material must comprise an overlayer, e.g. tin oxide, such that acidic sites on the support material are substantially blocked.

Existing processes suffer from a variety of issues impeding commercial viability including: (i) catalysts without requisite selectivity to ethanol; (ii) catalysts which are possibly prohibitively expensive and/or nonselective for the formation of ethanol and that produce undesirable by-products; (iii) required operating temperatures and pressures which are excessive; and/or (iv) insufficient catalyst life.

SUMMARY OF THE INVENTION

This invention is directed to use of a catalyst composition comprising at least one Group VIII metal, tin and from 0.01 to 0.5 wt. % cesium on a support comprising tungsten or oxides thereof in a process for manufacturing product comprising ethanol from feedstock comprising acetic acid and hydrogen under hydrogenation conditions including, for example, a temperature from 125° C. to 350° C. More preferably the catalyst may comprise from 0.05 to 0.2 wt. % cesium.

The catalyst composition for use herein comprises the at least one Group VIII metal, tin and from 0.01 to 0.5 wt. % cesium on the support comprising tungsten or oxides thereof, and which support may further comprises materials selected from the group consisting of silica, alumina, silica/alumina, calcium metasilicate, pyrogenic silica, high purity silica, titania, zirconia, zeolite, carbon, activated carbon, and mixtures thereof. In an embodiment of the invention, the support further comprises a support modifier selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In one embodiment the support modifier is preferably calcium metasilicate.

In another embodiment of the invention there is a process for producing ethanol that comprises contacting a feedstock comprising acetic acid and hydrogen in a suitable reaction zone at hydrogenation conditions including a temperature from 125° C. to 350° C. with a catalyst composition comprising at least one Group VIII metal, tin and from 0.01 to 0.5 wt. % cesium on a support comprising tungsten and oxides thereof. In another embodiment of the invention, the at least one Group VIII metal comprises iron, cobalt, nickel, ruthenium, rhodium, palladium, platinum or combinations thereof.

DETAILED DESCRIPTION OF THE INVENTION

The present invention relates to processes for producing a product comprising ethanol which comprises contacting a feedstock comprising acetic acid and hydrogen in a suitable reaction zone at hydrogenation conditions including a temperature from 125° C. to 350° C. with a catalyst composition comprising one or more active metals or oxides thereof that preferably includes a Group VIII metal. The Group VIII metal, for example, is selected from the group consisting of iron, cobalt, nickel, ruthenium, rhodium, palladium, platinum, osmium, iridium and combinations thereof. The one or more active metals in addition to the Group VIII metals may also preferably comprise chromium, tin, zinc, copper, and molybdenum. In addition to the one or more active metals, the catalyst may also comprise from 0.01 to 0.5 wt. % cesium, e.g., from 0.05 to 0.2 wt. % cesium, on a support material comprising tungsten or oxides thereof. For the purposes of determining the weight percent of the active metals on the catalyst, the weight of any oxygen that is bound to the metal is ignored.

The catalyst composition for use in the present invention comprises a support material comprising tungsten or oxides thereof. Preferably, the support comprises tungstic oxide ($WO_3$). In preferred embodiments, the support material is present in an amount from 25 wt. % to 99 wt. %, e.g., from 30 wt. % to 98 wt. % or from 35 wt. % to 95 wt. %, based on the total weight of the catalyst composition. The support materials may be selected from the group consisting of silica, alumina, silica/alumina, calcium metasilicate, pyrogenic silica, high purity silica, titania, zirconia, zeolite, carbon, activated carbon, and mixtures thereof.

The surface area of the support material comprising tungsten or oxides thereof preferably is at least 50 $m^2/g$, e.g., at least 100 $m^2/g$, at least 150 $m^2/g$, at least 200 $m^2/g$ or most preferably at least 250 $m^2/g$. In terms of ranges, the support material preferably has a surface area from 50 to 600 $m^2/g$, e.g., from 100 to 500 $m^2/g$ or from 100 to 300 $m^2/g$. For the purposes of the present specification, surface area refers to BET nitrogen surface area, meaning the surface area as determined by ASTM D6556-04, the entirety of which is incorporated herein by reference.

The support material comprising tungsten or oxides thereof also preferably has an average pore diameter from 5 to 100 nm, e.g., from 5 to 30 nm, from 5 to 25 nm or from 5 to 10 nm, as determined by mercury intrusion porosimetry, and an average pore volume from 0.5 to 2.0 $cm^3/g$, e.g., from 0.7 to 1.5 $cm^3/g$ or from 0.8 to 1.3 $cm^3/g$, as determined by mercury intrusion porosimetry.

The morphology of the support material comprising tungsten or oxides thereof, and hence of the catalyst composition for use herein, may vary widely. In some example embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the support material has a morphology that allows for a packing density from 0.1 to 1.0 $g/cm^3$, e.g., from 0.2 to 0.9 $g/cm^3$ or from 0.5 to 0.8 $g/cm^3$. In terms of size, the support material preferably has an average particle size, e.g., meaning the diameter for spherical particles or equivalent spherical diameter for non-spherical particles, from 0.01 to 1.0 cm, e.g., from 0.1 to 0.5 cm or from 0.2 to 0.4 cm. Since the one or more active metal(s) that are disposed on or within the support are generally very small in size, those active metals should not substantially impact the size of the overall catalyst particles. Thus, the above particle sizes generally apply to both the size of the support as well as the final catalyst particles.

As mentioned herein the catalyst support comprises tungsten or an oxide thereof and cesium. Without being bound by theory, cesium may be a promoter for tungsten that leads to an increase in catalyst activity and performance. In one embodiment, the amount of tungsten on the support may be from 0.1 to 50 wt. %, e.g., from 0.5 to 25 wt. %, from 1 to 20 wt. %, or from 4 to 16 wt. %. Although the weight ratio of cesium to tungsten may vary, it preferred that there is at least 0.05 wt. % cesium on the catalyst. This may vary with the amount of tungsten, but generally is effective in amounts up to 2 wt. % cesium. In some embodiments, tungsten may be present in an excess concentration relative to the concentration of cesium.

In some optional embodiments, the support material comprising tungsten and oxides thereof may also comprise a support modifier. A support modifier may adjust the acidity of the support material. In one embodiment, support modifiers are present in an amount from 0.1 to 50 wt. %, e.g., from 0.2 to 25 wt. %, from 0.5 to 15 wt. %, or from 1 to 8 wt. %, based on the total weight of the catalyst composition.

For example, the acid sites, e.g. Brønsted acid sites, on the support material may be adjusted by the support modifier to favor selectivity to ethanol during the hydrogenation of acetic acid. The acidity of the support material may be adjusted by reducing the number or reducing the availability of Brønsted acid sites on the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In particular, the use of a modified support that adjusts the acidity of the support to make the support less acidic or more basic favors formation of ethanol over other hydrogenation products.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. Acidic support modifiers include those selected from the group consisting of $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $ZrO_2$, $Nb_2O_5$, $Ta_2O_5$, and $Al_2O_3$. The acidic modifier may also include those selected from the group consisting of $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). The calcium metasilicate may be in crystalline or amorphous form.

In some embodiments, there may be a basic modifier and an acidic modifier. $SiO_2$ and $CaSiO_3$ may both be used with the support material comprising tungsten or oxides thereof.

The catalysts of the invention preferably include one or more active metals or oxides thereof. The one or more active metals are selected from the group consisting of cobalt, copper, gold, iron, nickel, palladium, platinum, iridium, osmium, rhenium, rhodium, ruthenium, tin, zinc, lanthanum, cerium, manganese, chromium, vanadium, and molybdenum. The total metal loading of the one or more active metals is from 0.1 to 25 wt. %, e.g., from 0.5 to 20 wt. %, or from 0.6 to 5 wt. %. In one embodiment, the one or more active metals may include a precious metal that is selected from the group consisting of rhodium, rhenium, ruthenium, platinum, palladium, osmium, iridium and gold. The precious metal may be in elemental form or in molecular form, e.g., an oxide of the precious metal. It is preferred that the catalyst comprises such precious metals in an amount less than 5 wt. %, e.g., less than 3 wt. %, less than 1 wt. % or less than 0.5 wt. %. In terms of ranges, the catalyst may comprise the precious metal in an amount from 0.05 to 10 wt. %, e.g. from 0.1 to 5 wt. %, or from 0.1 to 3 wt. %, based on the total weight of the catalyst.

In another embodiment, the catalyst may comprise two active metals or three active metals. The first metal or oxides thereof may be selected from the group consisting of cobalt, rhodium, rhenium, ruthenium, platinum, palladium, osmium, iridium and gold. The second metal or oxides thereof may be selected from the group consisting of copper, iron, tin, cobalt, nickel, zinc, and molybdenum. The third metal or oxides thereof, if present, may be selected from the group consisting of copper, molybdenum, tin, chromium, iron, cobalt, vanadium, palladium, platinum, lanthanum, cerium, manganese, ruthenium, rhenium, gold, and nickel. Preferably, the third metal is different than the first metal and the second metal. In addition, the first metal and the second metal may be different, and the third metal and the second metal may be different.

The metal loadings of the first, second, and optionally third metals are as follows. The first active metal may be present in the catalyst in an amount from 0.05 to 20 wt. %, e.g. from 0.1 to 10 wt. %, or from 0.5 to 5 wt. %. The second active metal may be present in an amount from 0.05 to 20 wt. %, e.g., from 0.1 to 10 wt. %, or from 0.5 to 5 wt. %. The third metal, when present, may be present in the catalyst in an amount from 0.05 to 20 wt. %, e.g. from 0.1 to 10 wt. %, or from 0.1 to 5 wt. %. The active metals may be alloyed with one another or may comprise a non-alloyed metal solution, a metal mixture or be present as one or more metal oxides. For purposes of the present specification, unless otherwise indicated, weight percent is based on the total weight the catalyst including metal and support.

Bimetallic catalysts for some exemplary catalyst compositions, excluding cesium and tungsten on the support, include platinum/tin, platinum/ruthenium, platinum/rhenium, platinum/cobalt, platinum/nickel, palladium/ruthenium, palladium/rhenium, palladium/cobalt, palladium/copper, palladium/nickel, ruthenium/cobalt, gold/palladium, ruthenium/rhenium, ruthenium/iron, rhodium/iron, rhodium/cobalt, rhodium/nickel, cobalt/tin, and rhodium/tin. More preferred bimetallic catalysts include platinum/tin, platinum/cobalt, platinum/nickel, palladium/cobalt, palladium/copper, palladium/nickel, ruthenium/cobalt, ruthenium/iron, rhodium/iron, rhodium/cobalt, rhodium/nickel, cobalt/tin, and rhodium/tin.

In some embodiments, the catalyst may be a tertiary catalyst that comprises three active metals on a support. Exemplary tertiary catalysts, excluding cesium and tungsten on the support, may include palladium/tin/rhenium, palladium/cobalt/rhenium, palladium/nickel/rhenium, palladium/cobalt/tin, platinum/tin/palladium, platinum/tin/rhodium, platinum/tin/gold, platinum/tin/iridium, platinum/cobalt/tin, platinum/tin/chromium, platinum/tin/copper, platinum/tin/zinc, platinum/tin/nickel, rhodium/nickel/tin, rhodium/cobalt/tin and rhodium/iron/tin. More preferably, a tertiary catalyst comprises three active metals may include palladium/cobalt/tin, platinum/tin/palladium, platinum/cobalt/tin, platinum/tin/chromium, platinum/tin/copper, platinum/tin/nickel, rhodium/nickel/tin, rhodium/cobalt/tin and rhodium/iron/tin.

Preferably, one or more of the active metals is selected from the Group VIII metals. The Group VIII metal may be selected from the group consisting of iron, cobalt, nickel, ruthenium, rhodium, platinum, palladium, osmium, iridium and combinations thereof. Additional active metals may also be used in some embodiments. Therefore, non-limiting examples of active metals on the present catalyst composition with cesium include platinum/tin/cesium, palladium/tin/cesium, platinum/palladium/tin/cesium, nickel/tin/cesium, platinum/nickel/tin/cesium, iron/platinum/tin/cesium, etc. The active metals may be alloyed with one another or may comprise non-alloyed metal solutions or mixtures.

Process for Making Catalyst

In one embodiment of making the catalyst composition for use herein, one or more support modifiers, if desired, may be added to the support material comprising cesium and tungsten or oxides thereof by mixing or through impregnation. Powdered materials of the modified support or a precursor thereto may be pelletized, crushed and sieved. Drying may also be preformed after the support modifier is added.

The modified or unmodified support material chosen for the catalyst composition may be shaped into particles having the desired size distribution, e.g., to form particles having an average particle size in the range from 0.2 to 0.4 cm. The support may be extruded, pelletized, tabletized, pressed, crushed or sieved to the desired size distribution. Any of the known methods to shape the support material into desired size distribution can be employed.

In a preferred method of preparing the catalyst, the active metals are impregnated onto the modified or unmodified support material comprising tungsten or oxides thereof. A precursor of the active metal preferably is used in the metal impregnation step, such as a water soluble compound or water dispersible compound/complex that includes the metal of interest. Depending on the metal precursor employed, the use of a solvent, such as water, glacial acetic acid or an organic solvent may be preferred. The next active metal also preferably is impregnated into the support material from a next metal precursor, and so forth. If desired, additional metal precursors may also be impregnated into the support material.

Impregnation occurs by adding, optionally drop wise, any or all the metal precursors, preferably in suspension or solution, to the dry support material comprising tungsten or oxides thereof. The resulting mixture may then be heated, optionally under vacuum, in order to remove the solvent. Additional drying and calcining may then be performed, optionally with ramped heating, to form the final catalyst composition. Upon heating and/or the application of vacuum, the metals of the metal precursors preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of the active metals (and optional additional metals) into the support material comprising tungsten or oxides thereof may occur simultaneously (co-impregnation)

or sequentially. In simultaneous impregnation, the metal precursors (and optionally additional metal precursors) are mixed together and added to the support material together, followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the active metal precursors in the event the two precursors are incompatible with the desired solvent, e.g., water.

In sequential impregnation, the first metal precursor is first added to the support material followed by drying and calcining, and the resulting material is then impregnated with the next metal precursor followed by an additional drying and calcining step to form the final catalyst composition. Additional metal precursors may be added either with the first and/or next metal precursor or a separate third impregnation step, followed by drying and calcination. Combinations of sequential and simultaneous impregnation may be employed if desired.

Suitable metal precursors include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, and sodium platinum chloride. A suitable tin precursor is stannous oxalate. A non-limiting example of a suitable compound for cesium precursors includes $CsNO_3$. Generally, both from the point of view of economics and environmental aspects, aqueous solutions of soluble compounds of platinum are preferred. In one embodiment, the metal precursor is not a metal halide and is substantially free of metal halides. A particularly preferred precursor to platinum is platinum ammonium nitrate, $Pt(NH_3)_4(NO_4)_2$. Calcining of the solution with the support and active metal may occur, for example, at a temperature from 250° C. to 800° C., e.g., from 300 to 700° C. or 500° C., optionally for a period from 1 to 12 hours, e.g., from 2 to 10 hours, from 4 to 8 hours or 6 hours.

Process for Hydrogenating Acetic Acid

One advantage of the catalyst for use in the present invention comprising at least one Group VIII metal, tin and from 0.01 to 0.5 wt. % cesium on a support material comprising tungsten or oxides thereof is the stability or activity of the catalyst for producing ethanol. Accordingly, it can be appreciated that the catalyst for use in the present invention is fully capable of being used in commercial scale industrial applications for hydrogenation of acetic acid, particularly in the production of ethanol. In particular, it is possible to achieve a degree of stability such that catalyst activity will have a rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

The raw materials, e.g. acetic acid and hydrogen, fed to the reaction zone used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol and ethyl acetate may be integrated with such processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g. lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolyzed with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid feedstock fed to the hydrogenation reaction zone may also comprise other carboxylic acids and anhydrides, as well as aldehyde and/or ketones, such as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reaction zone, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalyst may be used in conjunction with an inert material to regulate the pressure drop of the reactant stream through the catalyst bed and the contact time of the reactant compounds with the catalyst particles.

The hydrogenation in the reactor may be carried out in either liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 2100 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 500 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalyst bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from 100:1 to 1:100, e.g., from 50:1 to 1:50, from 20:1 to 1:2, or from 18:1 to 8:1. Most preferably, the molar ratio of hydrogen to acetic acid is greater than 2:1, e.g., greater than 4:1 or greater than 8:1. Generally, the reactor may use an excess of hydrogen, while a secondary hydrogenation reactor may use a sufficient amount of hydrogen as necessary to hydrogenate the impurities. In one aspect, a portion of the excess hydrogen from the reactor is directed to a secondary reactor for hydrogenation. In some optional embodiments, a secondary reactor could be operated at a higher pressure than the hydrogenation reactor and a high pressure gas stream comprising hydrogen may be separated from such secondary reactor liquid product in an adiabatic pressure reduction vessel, and the gas stream could be directed to the hydrogenation reactor system.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

For purposes of the present invention, the term "conversion" refers to the amount of acetic acid in the feed that is converted to a compound other than acetic acid. Conversion is expressed as a percentage based on acetic acid in the feed. The conversion may be at least 30%, e.g., at least 40%, or at least 60%. As stated above, the conversion with sequentially prepared catalyst is greater than the conversion with a simultaneously prepared catalyst. Although catalysts that have high conversions are desirable, such as at least 60%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mol. % of the converted acetic acid is converted to ethanol, we refer to the ethanol selectivity as 60%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. In terms of ethanol, for example, a productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Ethanol may be recovered from the product produced by the present process using suitable separation techniques.

The ethanol separated from the product of the process may be an industrial grade ethanol comprising from 75 to 96 wt. % ethanol, e.g., from 80 to 96 wt. % or from 85 to 96 wt. % ethanol, based on the total weight of the ethanol product. In some embodiments, when further water separation is used, the ethanol product preferably contains ethanol in an amount that is greater than 97 wt. %, e.g., greater than 98 wt. % or greater than 99.5 wt. %. The ethanol product in this aspect preferably comprises less than 3 wt. % water, e.g., less than 2 wt. % or less than 0.5 wt. %.

The ethanol produced by the embodiments of the present invention may be used in a variety of applications including fuels, solvents, chemical feedstocks, pharmaceutical products, cleansers, sanitizers, hydrogenation transport or consumption. In fuel applications, the ethanol may be blended with gasoline for motor vehicles such as automobiles, boats and small piston engine aircraft. In non-fuel applications, the ethanol may be used as a solvent for toiletry and cosmetic preparations, detergents, disinfectants, coatings, inks, and pharmaceuticals. The ethanol and ethyl acetate may also be used as a processing solvent in manufacturing processes for medicinal products, food preparations, dyes, photochemicals and latex processing.

The ethanol may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the ethanol may be esterified with acetic acid. In another application, the ethanol may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least 0.6 nm, and preferred zeolites include dehydration catalysts selected from the group consisting of mordenite, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

The following examples describe the catalysts and processes of this invention.

EXAMPLES

$WO_3$-Modified $SiO_2$ Supports

All example catalyst supports were prepared using the following procedure. A solution of 3.38 g of ammonium metatungstate (AMT) and 22.5 mL water was impregnated onto 20.0 g of 3 mm pellets of $SiO_2$ (3 mm support 61138, N or Pro) using an incipient wetness technique. The support material for the catalysts comprising 14% $WO_3$ and 86% $SiO_2$ was then dried using a rotor-evaporator and placed in an oven for 6 hours at 120° C. Finally, the support was calcined under flowing air at 550° C. for 6 hours.

All example stock solutions were prepared using the following procedure. A stock solution of 0.24 $g_{salt}$/mL, of Sn in water was prepared by dissolving 0.21 g of $SnC_2O_4$ and 0.376 g of $NH_4OX$ in 5.5 mL of $H_2O$. A stock solution of 0.2 $g_{salt}$/mL, of Pt was prepared by diluting 1.10 g $PtC_2O_4$ in 5.5 mL $H_2O$. A stock solution of 0.015 $g_{salt}$/mL, of Cs was prepared by dissolving 0.030 g of $CsNO_3$ in 11 mL of $H_2O$. [check solution concentrations]

Catalysts A, Comparative B: Pt and Sn Catalysts

Catalyst A: First, the Cs stock solution was impregnated on 9.90 g of the tungstic oxide modified support to create a metal loading of 0.1 wt. %. The resulting solid was the dried at 120° C. for 6 hours. Next, equal volumes of the Pt and Sn stock solutions were mixed and stirred at room temperature for 15 minutes. This mixture was impregnated on the solid to create a metal loading of 1.2 wt. % Sn and 1 wt. % Pt, and the resulting catalyst was then dried on a rotor-evaporator and then in an oven for 6 hours at 120° C. Finally, the catalyst was calcined at 300° C. for 6 hours. Catalyst A comprises 1 wt. % Pt, 1.2 wt. % Sn and 0.1 wt. % Cs on a support comprising 14 wt. % $WO_3$.

Comparative Catalyst B: First, equal volumes of the Pt and Sn stock solutions were mixed and then stirred at room temperature for 15 minutes. Next, this mixture was impregnated on 9.90 g of the support to create a metal loading of 1.2 wt. % Sn and 1 wt. % Pt, and the resulting catalyst was then dried on a rotor-evaporator and then in an oven for 6 hours at 120° C. Finally, the catalyst was calcined at 300° C. for 6 hours.

Catalyst B comprises 1 wt. % Pt, and 1.2 wt. % Sn on a support comprising 14 wt. % $WO_3$.

Catalysts C, Comparative D: Pt/Pd and Sn Catalysts

Catalyst C: First, the Cs stock solution was impregnated on 9.90 g of the tungstic oxide modified support to create a metal loading of 0.1 wt. %. The resulting solid was the dried at 120° C. for 6 hours. Then, 0.020 g of $Pd(NO_3)_2$ was added to the 5.5 mL of Pt stock solution. Next, equal volumes of the Pt/Pd and Sn stock solutions were mixed and stirred at room temperature for 15 minutes. This mixture was impregnated on the solid to create a metal loading of 1.2 wt. % Sn, 1 wt. % Pd and 1 wt. % Pt, and the resulting catalyst was then dried on a rotor-evaporator and then in an oven for 6 hours at 120° C. Finally, the catalyst was calcined at 300° C. for 6 hours. Catalyst C comprises 1 wt. % Pt, 1 wt. % Pd, 1.2 wt. % Sn and 0.1 wt. % Cs on a support comprising 14 wt. % $WO_3$.

Comparative Catalyst D: First, 0.02 g of $Pd(NO_3)_2$ was added to the 5.5 mL of Pt stock solution. Next, equal volumes of the Pt/Pd and Sn stock solutions were mixed and stirred at room temperature for 15 minutes. This mixture was impregnated on the solid to create a metal loading of 1.2 wt. % Sn, 1 wt. % Pd and 1 wt. % Pt, and the resulting catalyst was then dried on a rotor-evaporator and then in an oven for 6 hours at 120° C. Finally, the catalyst was calcined at 300° C. for 6 hours. Catalyst D comprises 1 wt. % Pt, 1 wt. % Pd, and 1.2 wt. % Sn on a support comprising 14 wt. % $WO_3$.

Table 1 summarizes the catalysts prepared. The active metal contents in wt. % are indicated for each of the catalysts.

TABLE 1

| Catalyst | Support | Pt wt. % | Pd wt. % | Sn wt. % | Cs wt. % |
|---|---|---|---|---|---|
| A | $WO_3/SiO_2$ | 1 | 0 | 1.2 | 0.1 |
| Comp. B | $WO_3/SiO_2$ | 1 | 0 | 1.2 | 0 |
| C | $WO_3/SiO_2$ | 1 | 1.2 | 1.2 | 0.1 |
| Comp. D | $WO_3/SiO_2$ | 1 | 1.2 | 1.2 | 0 |

Conversion Examples

Catalysts A, B, C, and D were placed in separate reactor vessels and dried by heating at 120° C. Feedstock acetic acid vapor was charged to the reactor vessels along with hydrogen and helium as a carrier gas with an average combined gas hourly space velocity (GHSV) of 2430 $hr^{-1}$, a temperature of 250° C., a pressure of 2500 kPa, and mole ratio of hydrogen to acetic acid of 8:1. Product samples are taken and analyzed at 20, 40, and 60 minutes of reaction time to determine conversion and selectivity. Analysis of the products is carried out by online gas chromatograph (GC). A three channel compact GC equipped with one flame ionization detector (FID) and 2 thermal conducting detectors (TCD) is used to analyze the feedstock reactant and reaction products. The front channel is equipped with an FID and a CP-Sil 5 (20 m)+WaxFFap (5 m) column and is used to quantify: acetaldehyde; ethanol; acetone; methyl acetate; vinyl acetate; ethyl acetate; acetic acid; ethylene glycol diacetate; ethylene glycol; ethylidene diacetate; and paraldehyde. The middle channel is equipped with a TCD and Porabond Q column and is used to quantify: $CO_2$; ethylene; and ethane. The back channel is equipped with a TCD and Porabond Q column and is used to quantify: helium; hydrogen; nitrogen; methane; and carbon monoxide.

Table 2 summarizes the results of the conversion examples. Conversion of acetic acid to product and selectivity to ethanol are reported at 20, 40, and 60 minutes of elapsed run time.

TABLE 2

| | HOAc Conversion (%) | | | EtOH Selectivity (%) | | |
|---|---|---|---|---|---|---|
| Catalyst | 20 min | 40 min | 60 min | 20 min | 40 min | 60 min |
| A | 58 | 68 | 70 | 66 | 64 | 65 |
| Comp. B | 26 | 26 | 26 | 40 | 37 | 35 |
| C | 65 | 75 | 80 | 64 | 64 | 63 |
| Comp. D | 40 | 50 | 53 | 62 | 60 | 60 |

It is observed from these examples that Catalyst A and C comprising at least one Group VIII metal, tin and from 0.01 to 0.5 wt. % cesium on a support material comprising tungsten or oxides thereof demonstrate superior performance over Comparative Catalysts B and D in terms of acetic acid conversion and ethanol selectivity.

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the foregoing descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

We claim:

1. A process for producing ethanol, comprising:
   hydrogenating acetic acid in the presence of a catalyst comprising one or more active metals, and cesium on a support comprising tungsten or oxides thereof.

2. The process of claim 1, wherein the catalyst comprises from 0.01 to 0.5 wt. % cesium.

3. The process of claim 1, wherein the catalyst comprises from 0.05 to 0.2 wt. % cesium.

4. The process of claim 1, wherein the one or more active metals is selected from the group consisting of iron, cobalt, nickel, ruthenium, rhodium, palladium, osmium, iridium, platinum and combinations thereof.

5. The process of claim 4, wherein the one or more active metals is selected from the group consisting of palladium, iron, cobalt, platinum and combinations thereof.

6. The process of claim 1, wherein acetic acid conversion is greater than 30%.

7. The process of claim 1, wherein the hydrogenation conditions include a temperature from 125 to 350° C., a pressure of 10 kPa to 3000 kPa and a hydrogen to acetic acid molar ratio of greater than 2:1.

8. The process of claim 1, wherein the support material further comprises silica, alumina, silica/alumina, calcium metasilicate, pyrogenic silica, high purity silica, titania, zirconia, zeolite, carbon, activated carbon, or mixtures thereof.

9. The process of claim 1, wherein the catalyst comprises tungsten in an amount from 0.1 to 50 wt. %, based on the total weight of the catalyst composition.

10. The process of claim 1, wherein the support material is present in an amount from 25 to 99 wt. %, based on the total weight of the catalyst composition.

11. The process of claim 1, wherein the support material further comprises a support modifier.

12. The process of claim 11, wherein the support modifier is present in an amount from 0.1 to 50 wt. %, based on the total weight of the catalyst composition.

13. The process of claim 11, wherein the support modifier is selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

14. The process of claim 11, wherein the support modifier is selected from the group consisting of oxides and metasilicates of sodium, potassium, magnesium, calcium, scandium, yttrium, zinc, and mixtures thereof.

15. The process of claim 14, wherein the support modifier is calcium metasilicate.

16. The process of claim 11, wherein the support modifier is selected from the group consisting of $ZrO_2$, $Nb_2O_5$, $Ta_2O_5$, $Al_2O_3$, $B_2O_3$, $P_2O_5$, $Sb_2O_3$, $MoO_3$, $Fe_2O_3$, $Cr_2O_3$, $V_2O_5$, $MnO_2$, $CuO$, $Co_2O_3$, $Bi_2O_3$, and combinations thereof.

17. The process of claim 1, wherein the support material has a surface area from 50 to 600 $m^2/g$.

18. The process of claim 1, further comprising gasifying a carbonaceous material to produce components of the feedstock.

19. The process of claim 18, wherein the carbonaceous material is selected from the group consisting of oil, coal, natural gas and biomass.

20. A process for producing product comprising ethanol which comprises contacting a feedstock comprising acetic acid and hydrogen in a reaction zone at hydrogenation conditions including a temperature from 125 to 350° C., a pressure of 10 kPa to 3000 kPa and a hydrogen to acetic acid molar ratio of greater than 2:1, with a catalyst composition comprising platinum, palladium or a combination thereof, tin and from 0.01 to 0.5 wt. % cesium on a silica support material comprising from 0.1 to 50 wt. % tungsten or oxides thereof.

21. A process for producing ethanol, comprising:

hydrogenating acetic acid in the presence of a catalyst comprising a Group VIII metal, tin, and cesium on a support comprising tungsten or oxides thereof, wherein the Group VIII metal is selected from the group consisting of iron, cobalt, nickel, ruthenium, rhodium, palladium, platinum, osmium, iridium and combinations thereof.

22. The process of claim 21, wherein the catalyst comprises from 0.01 to 0.5 wt. % cesium.

23. The process of claim 21, wherein the catalyst comprises from 0.1 to 50 wt. % tungsten or oxides thereof.

* * * * *